United States Patent [19]

Ekwall

[11] Patent Number: 4,899,750
[45] Date of Patent: Feb. 13, 1990

[54] LEAD IMPEDANCE SCANNING SYSTEM FOR PACEMAKERS

[75] Inventor: Christer Ekwall, Spanga, Sweden
[73] Assignee: Siemens-Pacesetter, Inc., Sylmar, Calif.
[21] Appl. No.: 183,191
[22] Filed: Apr. 19, 1988
[51] Int. Cl.[4] ............................................. A61N 1/00
[52] U.S. Cl. .............................. 128/419 PG; 128/734
[58] Field of Search ................. 128/419 PT, 419 PG, 128/734, 733

[56] References Cited

U.S. PATENT DOCUMENTS

| | | | |
|---|---|---|---|
| 4,380,237 | 4/1983 | Newbower | 128/734 |
| 4,459,995 | 7/1984 | Conners et al. | 128/734 |
| 4,630,615 | 12/1986 | Yomtov | 128/734 |
| 4,674,518 | 6/1987 | Salo | 128/734 |
| 4,697,591 | 10/1987 | Lekholm et al. | 128/419 PG |
| 4,780,661 | 10/1988 | Bolomey et al. | 128/734 |

Primary Examiner—Francis Jaworski
Assistant Examiner—George Manuel
Attorney, Agent, or Firm—Bryant R. Gold; Leslie S. Miller; Lisa P. Weinberg

[57] ABSTRACT

A pacemaker lead analyzer for measuring impedance during standard operation of an implanted pacemaker. The analyzer makes separate measurements of lead impedance during each heart signal and each pacing pulse. A moving average of measured parameters is maintained and recurring deviations from the norms are noted in separate event counters for subsequent analysis of the noted events as possible indications of impending failure of an implanted lead.

32 Claims, 2 Drawing Sheets

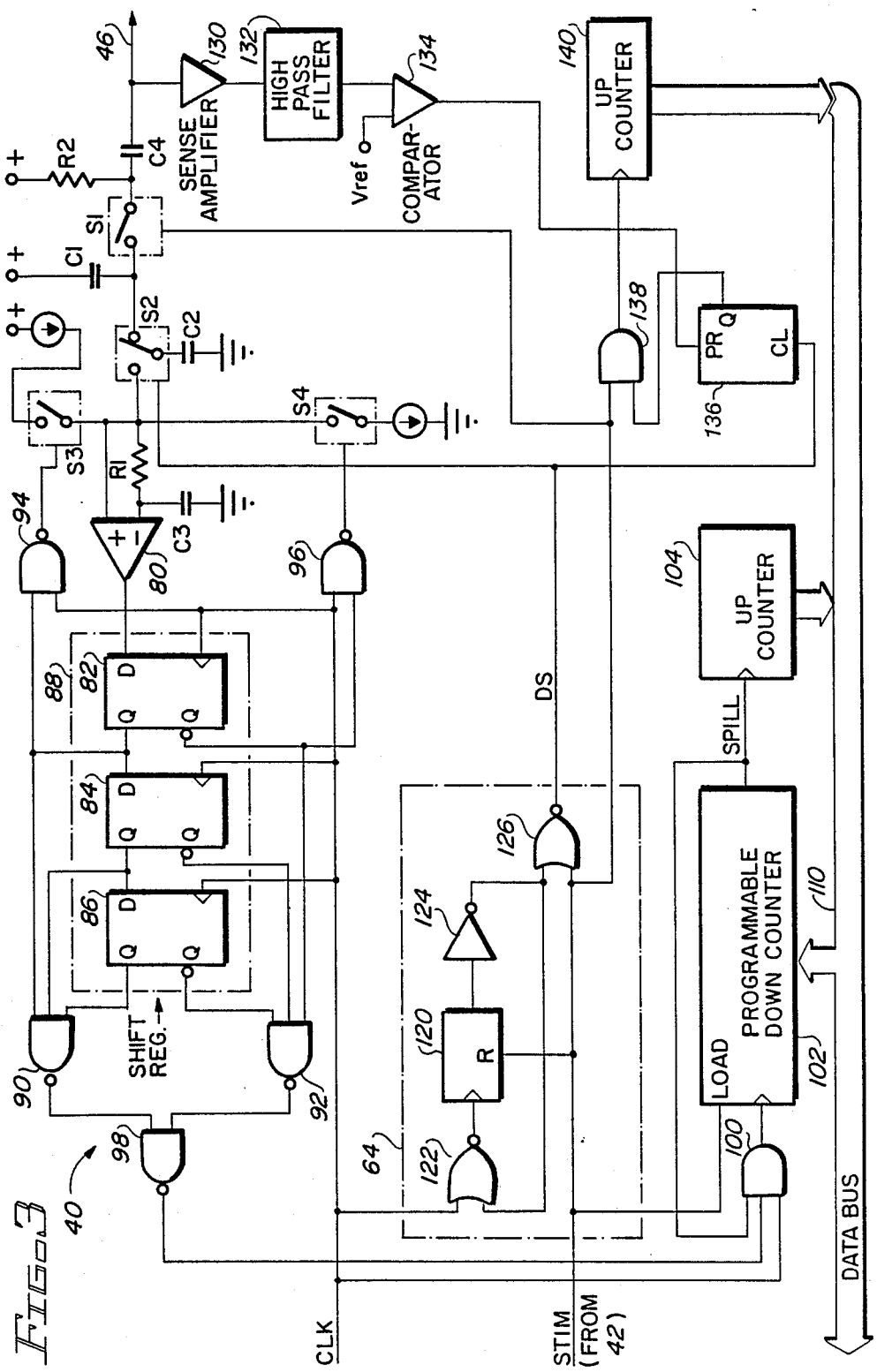

LEAD IMPEDANCE SCANNING SYSTEM FOR PACEMAKERS

This invention relates to body implantable systems for electrical stimulation of physiologic function and, more particularly, to electronic circuitry associated with pacemakers for monitoring implanted pacemaker operation and providing indications of detected departures from standard levels of selected parameters.

BACKGROUND OF THE INVENTION

The technology of cardiac pacemakers has developed to a high level of sophistication of system performance. The current generation of cardiac pacemakers incorporate microprocessors and related circuitry to sense and stimulate heart activity under a variety of physiological conditions. These pacemakers may be programmed to control the heart in correcting or compensating for various heart abnormalities which may be encountered in individual patients. A detailed description of modern cardiac pacemaker technology is set forth in International Application No. PCT/US85/02010, entitled STIMULATED HEART INTERVAL MEASUREMENT, ADAPTIVE PACER AND METHOD OF OPERATION, assigned to the assignee hereof. The disclosure of that application is incorporated herein by reference.

A demand-type pacemaker is one that provides a stimulation pulse only when the heart fails to produce a natural depolarization on its own within a prescribed escape interval. In a dual chamber pacemaker, this is realized by placing electrodes in both the right atrium and right ventricle of the heart. These electrodes are coupled through intravenous and/or epicardial leads to sense amplifiers housed in an implanted pacemaker. Electrical activity occurring in these chambers can thus be sensed. When electrical activity is sensed, the pacemaker assumes that a depolarization or contraction of the indicated chamber has occurred. If no electrical activity is sensed within a prescribed time interval, typically referred to as an atrial or ventricular escape interval, then a pulse generator, also housed within the pacemaker housing, generates a stimulation pulse that is delivered to the indicated chamber, usually via the same lead or electrode as is used for sensing. This stimulation pulse causes or forces the desired depolarization and contraction of the indicated chamber to occur. Thus, with a demand pacer, the heart will either beat on its own (without stimulation from the pacemaker) at a rate that is at least just slightly faster than the stimulation rate defined by the escape interval, or the heart will be stimulated by the pacer at a rate controlled by the escape interval. The stimulation rate provided by the pacemaker is typically referred to as the "programmed rate."

As noted, most pacemakers include a sensor circuit that looks for electrical signals from spontaneous heart activity. On detection of such activity, the pacemaker stimulation action is modified, depending upon the functional mode or type of pacemaker. For example, in the VVI mode (ventricle paced and sensed, response inhibited mode), sensing of heart activity under certain time restrictions is interpreted as normal heart activity such that the stimulating action is inhibited.

The discussion thus far has followed the assumption that a pacemaker and its associated circuitry operate without malfunction. By the very nature of manmade devices, such is not always the case. Whereas electronic circuitry can be, and is, incorporated within the pacemaker itself for exercising or testing various circuit components, the status of battery power sources, and the effectiveness of various amplifiers, waveform shaping stages and the like, it is often more difficult to test the integrity of the leads and implanted electrodes to which the pacemaker is coupled for pacing operation.

At the implanting of the pacemaker and electrode system, minor damage is sometimes incurred which may affect the system's electrical insulation. This type of damage may go undetected and be without present effect on the implanted system, but the condition may manifest itself after extended time in service. When a breakdown or significant degradation of the pacemaker lead insulation occurs, it can have serious or even disastrous results, depending upon whether or not the breakdown is of a catastrophic nature. Various types of lead damage may produce different types of failure or degradation. For example, an insulation defect on the stimulation electrode shunts the energy intended for the heart to some other point. A lead breakage can in some environmental situations temporarily or permanently reduce the stimulation output, sometimes drastically. Another type of detectable error relates to the failure of the electrode tip to be in proper contact with the heart wall.

While the lead defects which have been mentioned thus far are more in the nature of catastrophic failures, there may also occur failures or degradation of a less drastic nature which may be intermittent or which may build up over time. In a common situation, errors often start as temporary or intermittent errors. These can be virtually impossible to discover with commonly used techniques. It is not permissible to test on a random or periodic basis for lead faults in the manner in which power lines or telephone lines, for example, may be tested as, for example, by applying an over-voltage to a suspected circuit, simply because the breakdown of insulation in pacemaker leads under such condition may produce catastrophic results in the patient. It would be desirable to be able to use the signals encountered in the normal operation of an implanted pacemaker in the process analysis to determine impending failure or serious degradation from the temporary or intermittent errors which may be detected. A system for performing such a function would be expected to monitor standard heart operation and to use detected deviations or departures from signal norm to indicate the occurrence of such.

There may be various approaches to the regular monitoring of heart signals for the detection of abnormalities, some of which may relate to the circuitry employed in the implanted pacemaker system. One asserted pacemaker function analyzer for automatic evaluation and indication of the quality of performance of cardiac pacing systems is the subject of U.S. Pat. No. 4,527,567 of Fischler et al. The analyzer of that patent is said to provide a comprehensive examination of asynchronous, demand and demand-hysteresis pacemakers of all makes, including the state of the pacemaker's battery, the intactness of the electronic circuitry and of the electrodes, and the proper location of the electrodes in the heart. The manner in which this analysis is performed by the circuitry of that patent is entirely different from the operation of the lead impedance scanning system of the present invention.

PREFERRED EMBODIMENTS

Although the embodiments of the invention disclosed herein are shown and described in the context of a cardiac pacemaker, it should be understood that the invention is not limited thereto. The principles of the present invention may find application in connection with specific devices which are implanted for the purpose of providing electrical stimulation of other physiologic functions or of living animal tissue in general.

It should also be understood that the terms "lead impedance" and "lead resistance" as used herein are not to be limited with reference to specific electrical circuit leads only. Rather, these terms as used are intended to encompass impedance of both the circuit and lead-tissue interface, including body tissue and fluids and any interface effects which may be presented, for example, by the connection between an electrode tip and heart tissue.

SUMMARY OF THE INVENTION

In brief, arrangements in accordance with the present invention comprise electrical circuitry for monitoring signals transmitted via the pacemaker system leads and noting excessive variations in measured impedance. The monitoring provides a measurement of lead impedance with the occurrence of every heart stimulation pulse. Thus, not only are permanent lead abnormalities, such as insulation breakdown, lead breaks and the like, detected by arrangements in accordance with the present invention, but so also are lead impedance anomalies of a temporary or intermittent nature as well as significant but gradual variations in lead impedance which may be symptomatic of impending lead failure.

In one particular arrangement in accordance with the present invention, voltage level on a storage capacitor which is the source of heart stimulation pulses is sampled both before and after a stimulation pulse. The difference in voltage level between two such samples, due to the partial discharge of the storage capacitor resulting from the delivery of the stimulation pulse, is used to determine the instantaneous lead impedance which is a function of this voltage difference. The derived value is compared with a moving average of stored lead impedance measurements and an error counter is incremented if the current value differs from the moving average by a predetermined amount. Similarly, the output from the circuit of the pacemaker which is provided for sensing heart activity is used to monitor changes in sensed signals which may related to problems with leads involved in sensing. Any detected abnormality in the sensing lead results in the incremanting of a second error counter. The lead failure in this case is indicated as abnormal (unphysiological) sensed signal slew rates. For example, a lead fracture will momentarily provide step voltages or transient pulses with existing normal potentials between the body and conducting materials.

During a patient checkup, the count levels stored in the first and second error counters may be transferred to an appropriate test readout in order that attention may be directed to the fact that a possible lead problem exists.

BRIEF DESCRIPTION OF THE DRAWINGS

The above and other objects, features and advantages of the present invention will be more apparent from the following more particular description thereof presented in conjunction with the accompanying drawings, wherein:

FIG. 3 is a schematic circuit diagram showing further details of the arrangement of FIG. 2.

DETAILED DESCRIPTION OF THE INVENTION

The following description is of the best presently contemplated mode of carrying out the invention. This description is not to be taken in a limiting sense but is made for the purpose of describing the general principles of the invention. The scope of the invention should be determined with reference to the appended claims.

Figure 1:
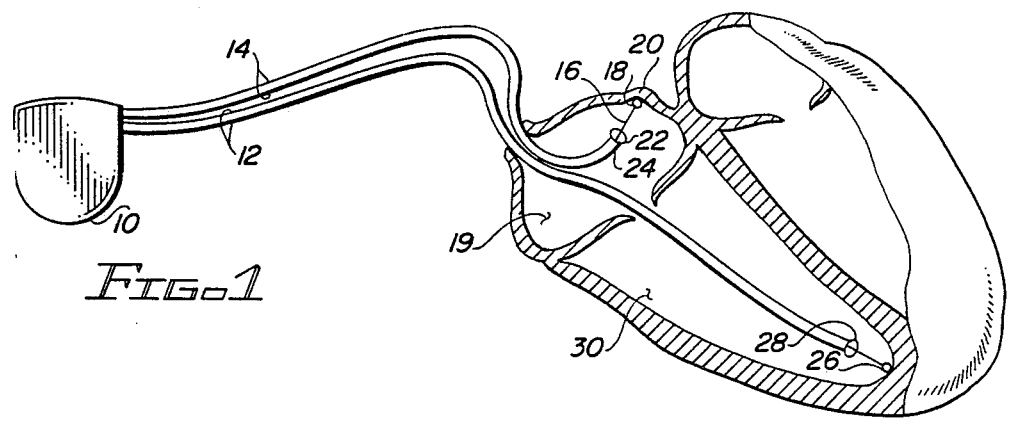
FIG. 1 is a schematic representation of a dual chamber cardiac pacemaker shown implanted in association with a heart for pacing.

Referring now to FIG. 1, there is shown a simplified representation of one way that an implanted pacemaker 10 may make electrical contact with the heart. FIG. 1 depicts the use of two bipolar leads 12 and 14, each being directed into a separate chamber of the right heart. A bipolar lead comprises a single fimilar that includes two electrically insulated conductors. For example, the lead 14 includes a first conductor 16 that is electrically connected to a distal tip 18 of the lead. This distal tip is typically placed in a cavity of the right atrium 19 referred to as the atrial appendage 20. A known distance from the distal tip 18 an electrode ring 22 is electrically connected to the other conductor 24 of the bipolar lead 14. Similarly, a distal tip 26 and a conductive ring 28 are associated with the bipolar lead 12 that is placed in the apex of the right ventricle 30. The manner in which the leads 12 and 14 are inserted into the heart, as well as the manner in which the pacemaker 10 is implanted in the body of a patient, are well known in the art.

The diagram of FIG. 1 may be considered to represent a rate-responsive pacer operating in the VVI mode if the bipolar lead 14 with its associated distal tip 18 and electrode ring 22 is eliminated from the figure so that only the bipolar lead 12 is left with its tip and ring 26, 28 inserted in the right ventricle 30, as shown in FIG. 1.

Figure 2:
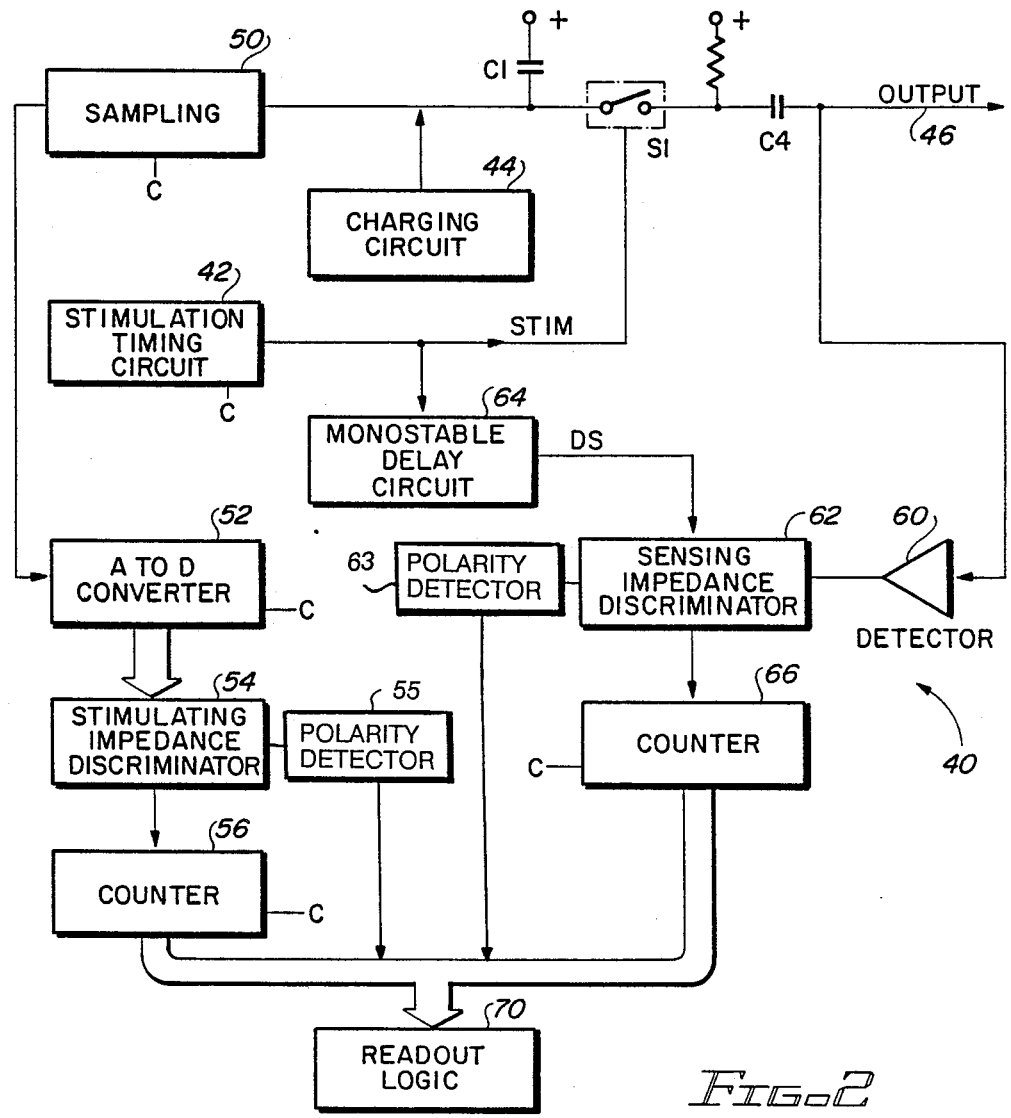
FIG. 2 is a schematic block diagram of one particular arrangement in accordance with the invention for incorporation in a pacemaker like that shown in FIG. 1.

A block diagram of a circuit in accordance with the present invention is shown in FIG. 2. The circuit 40 is shown comprising a stimulation timing circuit 42 which contains the normal pacemaker timing and logic circuitry. The stimulation timing circuit 42 is coupled to control the actuation of a switch S1 upon the occurrence of a stimulation signal STIM. The source of the pacing output at terminal 46 is a capacitor C1 which is coupled to be charged by a charging circuit 44 and which delivers the pacing pulse to the output 46 through a series capacitor C4 when the switch S1 is closed. Resistor R2 is provided to complete the circuit to capacitor C4 when switch S1 is open.

A sampling stage 50 is coupled to sample capacitor C1 before and after delivery of the pacing pulse. Sampled voltages from the sampling stage 50 are delivered to an analog-to-digital (A/D) converter 52, the output of which in digital form is applied to a stimulating impedance discriminator 54 which contains the circuitry for evaluating changes in lead impedance as a function of the voltage difference between the two levels sampled before and after delivery of a stimulation pulse corresponding to the following equation:

$$R = -T_p/(C_1 \ LN \ (1 - dV/V_o)) \quad (1)$$

where
- R represents a lead impedance,
- Tp is the stimulation pulse duration,
- C1 is the source capacitor for the stimulation pulse,
- Vo is the source voltage, and
- dV is the voltage difference between the two sampled values.

This equation is derived from the well-known relation with respect to time (t) for the voltage (v) across a discharging capacitor with initial voltage ($V_o$):

$$v = V_o \exp(-t/RC) \quad (2)$$

The stimulating impedance discriminator 54 maintains a moving average of lead impedance measurements according to Equation (1) and compares each new measurement with that average. If the measurement of lead impedance differs from the moving average by a predetermined value, an associated counter 56 is incremented to count the event as the occurrence of an error.

A polarity detector 55 is shown connected to the stimulating impedance discriminator 54 to provide an indication for the readout logic stage 70 of the direction of change for any differences in measurement of lead impedance which are detected by the stimulating impedance discriminator 54. Thus, for example, the polarity detector 55 provides an output indication of whether detected changes in lead impedance measurements involve an increase or decrease in impedance. This corresponds to an indication that lead degradation is in the direction of an open circuit (corresponding to measured increases in lead impedance) or in the direction of a short circuit (corresponding to a measured reduction in lead impedance).

A sensing detector 60 is coupled to the terminal 46 to respond to sensed heart activity. The output of the sensing detector 60 is applied to a sensing impedance discriminator 62 which receives a delayed signal DS from a monostable delay circuit 64 that is triggered by the STIM output of the stimulation timing circuit 42. This serves to prevent indication of high slew rate signals from stimulation output origin. The output of the sensing impedance discriminator 62 is applied to a second counter 66. The sensing impedance discriminator 62 responds to the slope (slew) of the signal from the sensing detector 60 such that when a rate of change greater than 10 volts per second is detected, the count in the counter 66 is incremented. A second polarity detector 63 is shown coupled to the sensing impedance discriminator 62 with an output being directed to the readout logic stage 70, in much the same fashion and for the same purpose as the polarity detector 55 which is connected to the stimulating impedance discriminator 54. The detector 63 provides an output indication of increasing impedance where the slope of the signal from the sensing detector 60 is positive and an output indication of decreasing impedance where the slope of that signal is negative. Thus, additional diagnostic information is provided at the readout logic stage 70 in response to polarity detectors 55, 63 over and above the mere indication of a detected change in lead impedance.

A readout logic stage 70 is coupled to the outputs of both counter stages 56 and 66 to provide an indication of the number of errors detected by the respective portions (stimulating signal and sensing signal) of the lead impedance analyzing circuit 40. The leads designated by the letter C indicate connections from the various stages to a system clock (not shown).

FIG. 3 represents the circuit 40 of FIG. 2 in more detailed schematic circuit form. In this figure, like elements have been given corresponding designations to those shown in FIG. 2.

In FIG. 3, the charging circuit 44 is represented as comprising a switch S2 and a capacitor C2, the latter having a small capacitance by comparison with C1. Thus, when capacitor C2 is connected to capacitor C1, as indicated with the condition of switch S2 shown in FIG. 3, C2 quickly assumes the voltage level of C1 without producing noticeable change therein. The circuit of R1 and C3 serves to create a moving average of the voltage level of C1, since C3 has a much greater capacitance than C2. Switches S3 and S4 are connected to provide alternating charge and discharge pulses to one input terminal of a first comparator stage 80 which is connected to receive at its other input the moving average of C1 voltage level. The output of the comparator 80 is coupled to the first stage 82 of a three-bit shift register 88, having additional stages 84 and 86. The outputs of the individual stages 82, 84, 86 are applied to three-terminal NAND gates 90, 92 while the outputs of the first stage 82 are additionally applied to two-input NAND gates 94, 96 which control switches S3 and S4. The outputs of the NAND gates 90, 92 are applied to a further NAND gate 98, the output of which is applied to one input of AND gate 100. An active output from gate 98 signifies the occurrence of an event corresponding to tee detection of three successive errors or anomalous impedance measurements. The output of AND gate 100 is coupled to a programmable down counter 102, which in turn is coupled to an up counter 104. The programmable down counter 102 is connected to be set to a predetermined value delivered over the data bus 110, the latter being connected to receive the count in the up counter 104.

The monostable delay circuit 64 of FIG. 2 comprises a flip flop 120 coupled to receive the output of an NOR gate 122 and to provide an output through a inverter amplifier 124 to another NOR gate 126. This serves to provide a delayed signal DS following a stimulation pulse from the stimulation timing circuit 42 of FIG. 2 in phase with a clock signal.

The sensing portion of the circuit comprises a sense amplifier 130 coupled to receive heart signals from terminal 46 and apply them through a high pass filter 132 to one input of a second comparator stage 134, the other input of which is coupled to a voltage reference Vref. The output of comparator stage 134 is applied to a flip flop 136, the output of which is applied, with the stimulation signal STIM, to an AND gate 138 which in turn is coupled to drive an up counter 140. The counter 140 is connected to provide data to the data bus 110.

In the operation of the circuit of FIG. 3, following a stimulating pulse from the stimulating timing circuit 42 (FIG. 2), the delayed DS signal is developed. During this time, capacitor C2 is connected to capacitor C1 via switch S2, and the same voltage level is developed on both capacitors C1 and C2. Alternation of the switch S2 transfers charge samples in bucket and dipper fashion from capacitor C1 to capacitor C3 in the moving average circuit to provide a voltage at one input of the comparator 80. As described in connection with FIG. 2, the stimulation pulse activates switch S1 to provide a pacing signal at terminal 46 from the capacitor C1. A momentary change of lead impedance in the lead connected to output terminal 46 creates a difference of potentials in capacitors C2 and C3 which is sensed by the comparator 80 and applied to the shift register 88 at input stage 82. If three consecutive deviation signals are applied to the shift register 88, gates 90, 92 and 98 are activated to develop a condition at the input to gate 100 signifying an event. This in phase with a clock pulse activates AND gate 100 to decrement the down counter 102. The counter 102 is set to a predetermined count value on receipt of a STIM signal. When the voltage difference between capacitor C2 and capacitor C3 exceeds a certain threshold value, the output of gate 98 is active long enough to develop the output from the programmable down counter 102, thereby incrementing the up counter 104.

A rapidly changing input signal to the sense amplifier 130 produces a voltage level at the comparator 134 which is higher than Vref. As a result, the signal from the comparator 134 sets the flip flop 136 if the DS signal is low. When this occurs at least once during a stimulating pulse interval, the next stimulating pulse from the stage 42 (FIG. 2) will increment the second counter 140. At pacemaker follow-up, the two counters 104 and 140 are read via the data bus 110. From the numbers read out of the counters 104 and 140, determinations of system performance, relative to the impedance condition of the pacer leads may be made.

As shown and described hereinabove, arrangements in accordance with the present invention monitor a prescribed pacemaker parameter related to the integrity of the implanted leads and keep a count according to the occurrences of a predetermined number of detected anomalies in succession. An anomaly is determined to be a deviation from the norm for that parameter by some predetermined amount. What constitutes the norm is determined from the operation of the system over time. Isolated anomalies corresponding to a single occurrence are disregarded, but if the particular anomaly persists over three heart beats, the occurrence of the event is recorded in a counter. Thus, at some later tine, such as during a routing patient checkup, for example, the contents of the counter may be noted so that a decision may be made with respect to whether or not the possible problem corresponding to the noted events needs to be corrected.

The preferred embodiment of the invention advantageously provides two distinct related systems for noting anomalies with respect to the testing of lead impedance. One system is based upon measurement of output energy delivered to the stimulation circuit during pacing; the other system involves the measurement of lead impedance from the monitoring of sensed heart signals. An analysis of the count readouts in the independent counters of both systems may further enhance the process of determining the particular lead problem which is indicated, particularly from a correlation of the separate count readouts as in the case of a pacemaker system which uses the same lead for sensing and pacing.

Although there have been described above specific arrangements of a lead impedance scanning system for pacemakers in accordance with the invention for the purpose of illustrating the manner in which the invention may be used to advantage, it will be appreciated that the invention is not limited thereto. Accordingly, any and all modifications, variations or equivalent arrangements which may occur to those skilled in the art should be considered to be within the scope of the invention as defined in the annexed claims.

What is claimed is:

1. A lead impedance scanning system for an implantable stimulation device for stimulating body tissue, the body tissue having an electrical impedance, said scanning system comprising:
   pulse generator means for generating stimulation pulses to the body tissue during a stimulation time interval;
   sensing means for sensing, during a sensing time interval, electrical signals generated by the body tissue;
   an implantable lead having an electrical impedance, said lead being implantable in the body tissue and coupled to said pulse generator means for delivering said stimulation pulses and to said sensing means for receiving said electrical signals; and
   detection means for detecting, during said simulation time interval and said sensing time interval, changes in combined impedance of said lead and of the body tissue at a point of contact of said lead with the body tissue.

2. The scanning system of claim 1, wherein a stimulation pulse is defined by said stimulation time interval and a stimulation pulse voltage, and wherein said detection means comprises:
   means for measuring said stimulation pulse voltage of a single stimulation pulse during said stimulation time interval; and
   impedance discriminating means for detecting lead impedance deviations derived from said measured stimulation pulse voltage.

3. The scanning system of claim 2, including a voltage source of known voltage value (Vo) and a first capacitor for providing said stimulation pulses, wherein said measuring means comprises:
   means for measuring a voltage change across said first capacitor during said stimulation time interval.

4. The scanning system of claim 3, wherein said impedance discriminating means comprises means for determining a lead impedance measurement, corresponding to said voltage change across said first capacitor, in accordance with the following equation:

$$R = -Tp/(C1 \text{ LN } (1 - dv/Vo))$$

where
   R represents the value of said lead impedance measurement,
   Tp represents the value of said stimulation time interval,
   C1 represents the value of said first capacitor,
   Vo represents the value of said voltage source, and
   dV represents the value of said voltage change across said first capacitor.

5. The scanning system of claim 4, wherein said impedance discriminating means further comprises:
   means for detecting an impedance measurement deviation when said lead impedance measurement is greater than a prescribed impedance value;
   polarity detecting means for detecting a direction of change of said impedance measurement deviation relative to said prescribed impedance value; and
   counter means for providing a count of impedance measurement deviations.

6. The scanning system of claim 3, wherein said impedance discriminating means comprises:
   means for detecting a voltage deviation corresponding to a lead impedance deviation when said voltage change across said first capacitor is greater than a reference voltage value.

7. The scanning system of claim 6, wherein said impedance discriminating means further comprises:
   means for generating a moving average of voltage deviations corresponding to lead impedance deviations, wherein said reference voltage value is equal to said moving average of voltage deviations.

8. The scanning system of claim 7, wherein said first capacitor is coupled to said moving average generating means by a charging circuit, said charging circuit comprises a second capacitor and a switch, said switch having a first and a second position, wherein said second capacitor samples the voltage across said first capacitor when said switch is in said first position, and said means for generating a moving average comprises:
   a resistor connected at one end to said second position of said switch; and
   a third capacitor, coupled between ground and the other end of said registor, wherein the voltage across said second capacitor is sampled by said third capacitor when said switch is in said second position and wherein the voltage across said third capacitor is held when said switch is in said first position, whereby the voltage across said third capacitor gradually accumulates the voltage value of said first capacitor.

9. The scanning system of claim 8, further comprising:
   counter means for counting at least one of said voltage deviations.

10. The scanning system of claim 8, further comprising:
    counter means for counting three successive voltage deviations.

11. The scanning system of claim 1, wherein said detection means comprises:
    impedance discriminating means for detecting nonphysiologic electrical signals, sensed during said sensing time interval, which are greater than 10 V/s.

12. The scanning system of claim 11, wherein said impedance discriminating means comprises:
    a voltage reference;
    a filter for passing high-frequency electrical signals sensed by said sensing means which are associated with nonphysiologic signals; and
    means for detecting a measurement deviation when the amplitude of said high-frequency electrical signals is greater than said voltage reference.

13. The scanning system of claim 12, further comprising:
    counter means for providing a count of measurement deviations.

14. An apparatus for measuring lead impedance of an implantable stimulation device for stimulating body tissue which has an electrical impedance, the apparatus comprising:
    means for measuring a stimulation pulse voltage over a single pulse;
    an impedance lead having an electrical impedance, said lead being implantable in the body tissue and coupled to said pulse generator means for delivering said stimulating pulse; and
    impedance discriminating means for determining a corresponding lead impedance measurement derived from said stimulation pulse voltage, said lead impedance measurement being the combined impedances of said lead and the body tissue.

15. The apparatus of claim 14, including a voltage source of known value (Vo) and a first capacitor for providing said stimulation pulses, each pulse having a known stimulation pulse interval, wherein said measuring means comprises:
    means for measuring a voltage change of said first capacitor during said stimulation pulse interval.

16. The apparatus of claim 15, wherein said impedance discriminating means further comprises means for determining said corresponding lead impedance measurement in accordance with the following equation:

$$R = -Tp/(C1 \text{ LN } (1-dV/Vo))$$

where
   R represents the value of said corresponding lead impedance measurement,
   Tp represents the value of said stimulation pulse interval,
   C1 represents the value of said first capacitor,
   Vo represents the value of said voltage source, and
   dV represents the value of said voltage change across said first capacitor.

17. A method of detecting the existence of a defective lead, said lead implanted in the body tissue and coupled to an implantable stimulation device which stimulates body tissue, said lead and the body tissue having an electrical impedance, comprising the steps of:
    generating stimulation pulses to the body tissue during a stimulation time interval;
    sensing electrical signals generated by the body tissue during a sensing time interval; and
    detecting, during said stimulation time interval and said sensing time interval, changes in the combined impedances of said lead and of the body tissue at the point of contact of said lead with the body tissue.

18. The method of claim 17, wherein said detecting step comprises the steps of:
    measuring a voltage during a single stimulation pulse delivered during said stimulation time interval; and
    detecting lead impedance deviations derived from the voltage of said stimulation pulse.

19. The method of claim 18, wherein said implantable stimulation device includes a voltage source of known voltage value (vo) and a first capacitor for providing said stimulation pulses, each pulse having a known stimulation time interval, wherein said measuring step comprises the step of:
    measuring a voltage change of said first capacitor during said stimulation time interval.

20. The method of claim 19, wherein said determining step comprises the step of determining a lead impedance measurement, corresponding to said voltage change of said first capacitor, in accordance with the following equation:

$$R = -Tp/(C1 \text{ LN } (1-dV/Vo))$$

where
   R represents the value of said lead impedance measurement,

Tp represents the value of said stimulation time interval,

C1 represents the value of said first capacitor,

Vo represents the value of said voltage source, and dV represents the value of said voltage change across said first capacitor.

21. The method of claim 20, wherein said step of detecting lead impedance deviations comprises the steps of:

providing an impedance reference;

comparing said lead impedance measurement to the value of said impedance reference; and indicating an impedance measurement deviation when said corresponding lead impedance measurement is greater than said impedance reference value.

22. The method of claim 21, further comprising the steps of:

detecting a direction of change of impedance relative to said impedance reference value; and counting at least one of said measurement deviations, whereby at least one of said measurement deviations provides an indicia of a defective lead.

23. The method of claim 19, wherein said step of detecting lead impedance deviations comprises the steps of:

providing a voltage reference; and detecting voltage deviations, corresponding to lead impedance deviations, whenever said voltage change across said first capacitor is greater than the value of said voltage reference.

24. The method of claim 23, wherein said step of providing a voltage reference comprises the step of:

generating a moving average, corresponding to lead impedance measurements, wherein said voltage reference equals said moving average.

25. The method of claim 24, further comprising the step of:

counting at least one of said measurement deviations, whereby at least one of said measurement deviations provides an indicia of a defective lead.

26. The method of claim 24, further comprises the step of:

counting at least three successive voltage deviations, whereby at least three successive voltage deviations provides an indicia of a lead impedance deviation.

27. The method of claim 17, wherein said detecting step comprises the step of:

detecting nonphysiologic electrical signals, sensed during said sensing time interval, which are greater than 10 V/s, thereby indicating an abnormal lead impedance.

28. The method of claim 27, wherein said nonphysiologic detecting step comprises the steps of:

providing a voltage reference;

passing high-frequency electrical signals, as sensed by said sensing means, said high-frequency electrical signals being associated with nonphysiologic signals; and detecting a measurement deviation when the amplitude of said high-frequency electrical signals is greater than said voltage reference.

29. The method of claim 28, further comprising the step of:

counting at least one of said measurement deviations, whereby at least one of said measurement deviations is an indicia of a defective lead.

30. A method of measuring the combined impedance of an implantable lead coupled to an implantable stimulation device and body tissue at the point of contact of said lead with said body tissue, comprising the steps of:

delivering stimulating pulses from said implantable stimulation device to said body tissue through said implantable lead;

measuring a single stimulation pulse voltage; and determining a corresponding lead impedance measurement derived from said single stimulation pulse voltage.

31. The method of claim 30, wherein said implantable stimulation device includes a voltage source of known voltage value (Vo) and a first capacitor for providing said stimulation pulses, each pulse having a known stimulation pulse interval, wherein said measuring step comprises the step of:

measuring a voltage change of said first capacitor during said stimulation pulse interval.

32. The method of claim 31, wherein said determining step further comprises the step of determining said corresponding lead impedance measurement in accordance with the following equation:

$$R = -Tp/(C1\ LN\ (1 - dV/Vo))$$

where

R represents the value of said corresponding lead impedance measurement,

Tp represents the value of said stimulation pulse interval,

C1 represents the value of said first capacitor,

Vo represents the value of said voltage source, and dv represents the value of said voltage change across said first capacitor.

* * * * *